United States Patent
Goeringer et al.

(10) Patent No.: US 12,278,011 B1
(45) Date of Patent: Apr. 15, 2025

(54) METHOD AND ARCHITECTURE IN SUPPORT OF PATIENT-CENTRIC NETWORKS

(71) Applicant: Cable Television Laboratories, Inc., Louisville, CO (US)

(72) Inventors: Steven Goeringer, Louisville, CO (US); Chris Riha, Louisville, CO (US); Darshak Thakore, Louisville, CO (US); Igor Faynberg, Louisville, CO (US)

(73) Assignee: Cable Television Laboratories, Inc., Louisville, CO (US)

( * ) Notice: Subject to any disclaimer, the term of this patent is extended or adjusted under 35 U.S.C. 154(b) by 642 days.

(21) Appl. No.: 17/356,320

(22) Filed: Jun. 23, 2021

Related U.S. Application Data (60) Provisional application No. 63/042,930, filed on Jun. 23, 2020.

(51) Int. Cl.
| | |
|---|---|
| *G16H 40/20* | (2018.01) |
| *G16H 10/60* | (2018.01) |
| *G16H 10/65* | (2018.01) |
| *G16H 20/10* | (2018.01) |
| *G16H 40/67* | (2018.01) |
| *G16H 50/20* | (2018.01) |
| *H04L 67/12* | (2022.01) |
| *H04W 84/12* | (2009.01) |

(52) U.S. Cl.
CPC ............. *G16H 40/20* (2018.01); *G16H 10/60* (2018.01); *G16H 10/65* (2018.01); *G16H 40/67* (2018.01); *G16H 20/10* (2018.01); *G16H 50/20* (2018.01); *H04L 67/12* (2013.01); *H04W 84/12* (2013.01)

(58) Field of Classification Search
CPC ........ G16H 40/20; G16H 40/67; G16H 10/60; G16H 10/65; G16H 50/20; G16H 20/10; H04L 67/12; H04W 84/12
See application file for complete search history.

(56) References Cited

U.S. PATENT DOCUMENTS

| | | | |
|---|---|---|---|
| 10,104,548 B1 * | 10/2018 | Dowlatkhah | H04W 8/24 |
| 2014/0022255 A1 * | 1/2014 | Barbouche | G16Z 99/00 |
| | | | 345/440 |
| 2018/0124029 A1 * | 5/2018 | Zibuschka | H04L 63/0823 |
| 2018/0234519 A1 * | 8/2018 | Boyapalle | H04L 67/06 |
| 2018/0293399 A1 * | 10/2018 | Chan | H04L 63/101 |
| 2020/0296136 A1 * | 9/2020 | Liu | H04L 63/02 |
| 2020/0366611 A1 * | 11/2020 | Kommula | H04L 45/22 |

(Continued)

*Primary Examiner* — Glenton B Burgess
*Assistant Examiner* — Jihad K Boustany
(74) *Attorney, Agent, or Firm* — Josh C. Snider; Snider IP (57) ABSTRACT

Network communication systems and methods implementing micro network subsystems for securely delivering personal electronic information across wired and/or wireless media are disclosed. Software-defined networking (SDN) is used to segment a provider network into a plurality of personal micro networks each established for an object that is cryptographically bound to or cryptographically associated with a living being. When multiple providers implementing different workflows and binding different objects to the same person are connected to the communication system, an interoperable network database stores the information and compiles, searches, and distributes the information to/from multiple providers.

20 Claims, 9 Drawing Sheets

(56) References Cited

U.S. PATENT DOCUMENTS

2021/0335488 A1* 10/2021 Higginson ............. H04B 17/27
2023/0170085 A1*  6/2023 Khawer ................. G16H 20/40
                                                      705/2

* cited by examiner

METHOD AND ARCHITECTURE IN SUPPORT OF PATIENT-CENTRIC NETWORKS

CROSS-REFERENCE TO RELATED APPLICATIONS

This application claims the benefit of and priority to U.S. Provisional Patent Application No. 63/042,930, filed Jun. 23, 2020, which is hereby incorporated by reference in its entirety.

STATEMENT REGARDING FEDERALLY SPONSORED RESEARCH

None.

BACKGROUND

Device and network management frameworks that organize connected devices on the network into trust domains by creating separate micro networks, or "micronets", are described for example in U.S. Patent Pub. No. 2020/0092254, which is hereby incorporated by reference in its entirety. The micronet framework provides dynamic and adaptive software defined networking (SDN)-driven controls to deliver secure services and routing between trust domains. SDN is used both to isolate traffic between various trust domains and to manage traffic flow. Micronet segmentation and trust domains may be used in a local network or may extend outside the on-premises network using SDN, Virtual Private Network (VPN), or other solutions. This allows a cable operator to connect specific devices to protected cloud services or be part of a larger software-defined network in a wide area network. The micronet framework therefore provides wide geographic and configurational versatility enabling the security of devices. This versatility is expanded further by the systems and methods disclosed herein.

SUMMARY

For purposes of illustration, the systems and methods disclosed herein are described in the context of medical services and medical information. However, the systems and methods disclosed herein may be applied to personal services and information in a variety of fields, including but not limited to the financial, educational, and legal fields.

Systems and methods for managing medical care address at least one of the following aspects.

The first aspect is episodic, as it involves the hospital operational workflows for the patient admission, initial prescription of care, assignment of devices (such as a bed, vital devices, etc.), and subsequent prescription of care (such as controlled medication administration through a pump).

The second aspect is payer-centric, as it involves the business workflows of a medical insurance enterprise, which needs to provide—possibly through a real-time interactive communication with health care providers—the necessary authorizations related to the episodic aspect.

The third aspect is patient-centric. It deals with the patient specifics.

Figure 1:
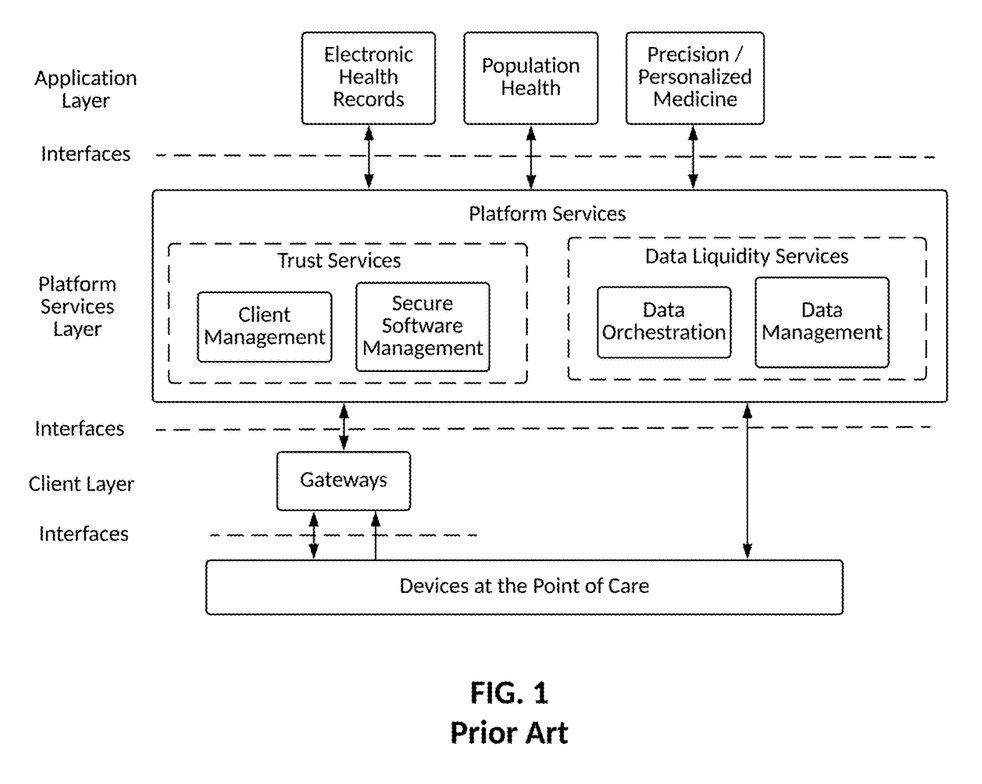
FIG. 1 is a schematic of the prior art CMI Reference Architecture.

The state of the prior art is reflected in FIG. 1, which depicts the model developed by the Center for Medical Interoperability (CMI). Its general architectural framework has three layers—the application layer, platform services layer, and client layer. The platform services layer provides two types of services—trust services (security for the client- and software-management) and data liquidity services (such as data orchestration and data management). The client layer provides the gateway to the devices at the point of care.

The CMI architectural framework has several gaps. For example, it does not address differentiated applications, it does not handle intelligence about health system processing, and it does not address the needs of a clinician; nor does it address the specific needs of per-patient care. More importantly, the CMI framework misses network-related aspects, such as software-defined networking (SDN), and related servers as well as basic network elements, such as access points, switches, routers, operations systems, etc.

To illustrate issues associated with an episodic case for a patient's admission to a medical facility, at which point a doctor prescribes the use of one or more devices and one or more prescriptions. Devices assigned to a patient can be used for monitoring (e.g., a non-invasive blood pressure monitor or an electric cardiogram) as well as for action (e.g., a medicine dispenser or an insulin pump). The devices to be used, as well as actions, are specified in the electronic health record (EHR) (e.g., using medical coding). Even though there is an electronic description of the devices and associated actions, all such patient-to-device and patient-to-prescription associations are made manually by medical personnel.

Reading and controlling the devices is typically done manually, naturally contributing to the accumulation of human error, particularly where event logs are required to assess performance over time. For devices that are remote-controllable, and perhaps attached to a hospital network, there is no universal mechanism for managing and controlling the devices.

When a patient, is moved to a different room, all stationary devices are replaced. Furthermore, when a patient is discharged-along with non-stationary devices (such as a medicine pump or heart monitor), there is no seamless handover. Even though network-capable devices can be attached to a network operator's managed network, via a wireless- or wireline interface, there is no uniform mechanism for enforcing, controlling, or operating over such an interface (which would also have to be arranged manually).

The present invention provides an overarching solution for emerging medical environments, in which tracking and administering a regulation-compliant patient treatment including administering prescribed medicine, is highly automated and programmable. A Patient-Centric Network (PCN) disclosed herein involves 1) federation of multiple identity management systems, 2) interworking of workflows that belong to independent business realms, and 3) programmability of the underlying networks over which the application's communications are carried. To this end, the entities that are involved as the end-points of an application (such as a patient, a payer, etc.) are defined within each of the federated realms along with the appropriate networking mechanisms.

In an aspect, a network communication system implementing a micro network subsystem for securely delivering personal electronic information across wired and/or wireless media comprises: a partner network including an interoperability platform that provides trust services and data liquidity services for the micro network platform; a micro network manager in operable communication with the interoperability platform and configured to orchestrate service delivery across the communication system and the micro network subsystem; a gateway in operable communication with the micro network manager, the gateway configured to implement a software defined networking (SDN) switch to automatically segment a provider network into a plurality of personal micro networks each established for an object that is cryptographically bound to a living being; and a database that registers the true identity of the living being with the cryptographically bound object.

In an embodiment, the micro network manager is located in the provider network or in a system operator network. In an embodiment, the gateway is located in the provider network or remote from the provider network. For example, the gateway may be remote from—yet securely connected to—the provider network via tunneling or a virtual privacy network (VPN) connection.

In an embodiment, the interoperability platform is a medical interoperability platform facilitating data services from one or more of a database that registers the true identities of living beings with their cryptographically bound objects, an electronic health record database, a medical financial system, clinical decision support systems, and academic cloud services.

In an embodiment, an object is selected from the group consisting of a bar code, a QR code, a radio frequency ID (RFID) tag, a Bluetooth® device, a near-field communication device, a Wi-Fi enabled device, and/or a personal computing device.

In an embodiment, a network communication system further comprises one or more additional or ancillary objects associated with each of the personal micro networks.

In an embodiment, the additional object(s) is/are medical provisions selected from the group consisting of a medical device, a medical provider, a medical payer, a prescription, a diagnosis, a bill, or a treatment protocol.

In an embodiment, an object may be a physical object or an electronic object, such as an electronic prescription or an electronic diagnosis, which may be medically coded.

In an embodiment, at least one of the additional objects comprises a canonical name including at least an object identifier and an object parameter list. The canonical name may further include an action list including instructions that when executed by a processor cause the additional object to perform a function. For example, the function may be to conduct a test (e.g., check a patient's blood pressure), report results, and/or notify a medical provider. A processor for receiving the instructions may be disposed within the additional object or within the PCN controller/micronet manager.

In an embodiment, a network communication system further comprises a translator for converting a canonical name into instructions for a workflow processor of a provider network.

In an embodiment, a database is a local database, a remote database, a distributed database, or a cloud database. In an embodiment, a database is an interoperable network database that compiles multiple objects cryptographically bound to each of the living beings by a plurality of provider networks and generates a comprehensive lifetime record of events. For example, a hospital, an insurer and a doctor's office may each create a micro network for a single person, where the person's identity is cryptographically bound to a different object in each case. The interoperable network database is configured to recognize data from each micro network as relating to a single living being and to compile the information into a single record or chain. In an embodiment, a database is a blockchain centralized database or a blockchain distributed database.

In an aspect, a method for securely delivering personal electronic information across wired and/or wireless media in a micro network subsystem of a network communication system comprises: establishing a micro network for an object that is cryptographically bound to a living being, thereby forming a personal micro network; providing a micro network manager in operable communication with an interoperability platform that provides trust services and data liquidity services, the micro network manager configured to orchestrate service delivery across the communication system and the micro network subsystem; and providing a gateway in operable communication with the micro network manager, the gateway configured to implement a software defined networking (SDN) switch to automatically segment the personal micro network from the network communication system.

In an embodiment, a method for securely delivering personal electronic information further comprises associating a true identity of a living being with a cryptographically bound object in a database. In an embodiment, a method for securely delivering personal electronic information further comprises associating one or more additional objects with the personal micro network.

In an embodiment, the living being is a human or a non-human animal.

In an embodiment, the personal electronic information is medical information, financial information, educational information and/or legal information.

In an embodiment, the additional or ancillary object(s) associated with a personal micro network is/are medical provisions selected from the group consisting of a medical device, a medical provider, a medical payer, a prescription, a diagnosis, a bill, or a treatment protocol.

In an embodiment, the additional or ancillary object(s) associated with a personal micro network is/are financial provisions selected from the group consisting of a financial institution, a financial advisor, a financial account or a loan.

In an embodiment, the additional or ancillary object(s) associated with a personal micro network is/are educational provisions selected from the group consisting of an educational institution, a curriculum, grades, test scores, letters of recommendation or a disciplinary record.

In an embodiment, the additional or ancillary object(s) associated with a personal micro network is/are legal provisions selected from the group consisting of a law firm, attorney-client correspondence, attorney work product, a judicial institution, a criminal record, judicial proceeding documents, a penal institution, a disciplinary record, a probation record or a parole officer.

In an embodiment, a method for securely delivering personal electronic information further comprises automatically disassociating one of the additional objects from the personal micro network when a new object having one or more specified matching parameters is associated with the personal micro network.

In an embodiment, a method for securely delivering personal electronic information further comprises searching for all of the objects or a subset of the objects associated with the personal micro network. For example, the search may identify the object most recently associated with the personal micro network.

In an embodiment, a method for securely delivering personal electronic information further comprises adding a new object to a chain of the objects associated with the personal micro network.

In an embodiment, a method for securely delivering personal electronic information further comprises setting permissions or authentication standards for access to the database.

In an aspect, a non-transitory computer-readable medium has a plurality of non-transitory instructions executable with a processor of a user equipment (UE) for securely delivering personal electronic information across wired and/or wireless media in a micro network subsystem of a network communication system, the plurality of non-transitory instructions being executable for: establishing a micro network for an object that is cryptographically bound to a living being, thereby forming a personal micro network; providing trust services and data liquidity services; orchestrating service delivery across the communication system and the micro network subsystem; and controlling a software defined networking (SDN) switch to automatically segment the personal micro network from the network communication system.

In an embodiment, the plurality of non-transitory instructions are further executable for associating a true identity of a living being with a cryptographically bound object in a database.

In an embodiment, the plurality of non-transitory instructions are further executable for associating one or more additional objects with the personal micro network. In an embodiment, the plurality of non-transitory instructions are further executable for automatically disassociating one of the additional objects from the personal micro network when a new object having one or more specified matching parameters is associated with the personal micro network.

In an embodiment, the plurality of non-transitory instructions are further executable for searching for all of the objects or a subset of the objects associated with the personal micro network. For example, the search may identify the object most recently associated with the personal micro network.

In an embodiment, the plurality of non-transitory instructions are further executable for adding a new object to a chain of the objects associated with the personal micro network.

In an embodiment, the plurality of non-transitory instructions are further executable for setting permissions or authentication standards for access to the database, and for enforcing the standards.

BRIEF DESCRIPTION OF THE DRAWINGS

Illustrative embodiments of the present invention are described in detail below with reference to the attached drawings, wherein.

DETAILED DESCRIPTION

In general, the terms and phrases used herein have their art-recognized meaning, which can be found by reference to standard texts, journal references and contexts known to those skilled in the art. The following definitions are provided to clarify their specific use in the context of this description.

As used herein, the term "network" refers generally to any type of telecommunications or data network including, without limitation, hybrid fiber coaxial (HFC) networks, satellite networks, telco networks, and data networks (including MANs, WANs, LANs, WLANs, internets, and intranets). Such networks or portions thereof may utilize any one or more different topologies (e.g., ring, bus, star, loop, etc.), transmission media (e.g., wired/RF cable, RF wireless, millimeter wave, optical, etc.) and/or communications or networking protocols (e.g., SONET, DOCSIS, IEEE Std. 802.3, ATM, X.25, Frame Relay, 3GPP, 3GPP2, 4G, 5G, LTE/LTE-A, WAP, SIP, UDP, FTP, RTP/RTCP, H.323, etc.).

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit (ASIC), and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

For the purposes of this description, a "micro network" or "micronet" may refer to an IP subnetwork, or subnet, assigned to one or more devices or objects. The assigned devices or objects may be uniquely identified by a subnet identifier within an IP address.

For purposes of this description, a "personal micro network" is a micro network assigned to an object that is cryptographically bound to a living being, such as a human or non-human animal.

The terms "direct and indirect" describe the actions or physical positions of one object relative to another object. For example, an object that "directly" acts upon or touches another object does so without intervention from an intermediary. Contrarily, an object that "indirectly" acts upon or touches another object does so through an intermediary (e.g., a third component).

Integrated, Seamless, and Automated Medical Applications Operating Over Programmable Networks The present disclosure teaches a medical interoperability platform that closes the gaps of the CMI model. The present systems and methods allow for the interworking of independent workflows via a mechanism that preserves modularity. The present systems and methods apply the Cable Labs Micronets approach, which is disclosed for example in U.S. patent application Ser. Nos. 16/664,657, 16/576,747, 16/556,219, 16/120,063, and 15/443,855, each of which is hereby incorporated by reference herein in its entirety.

Figure 2:
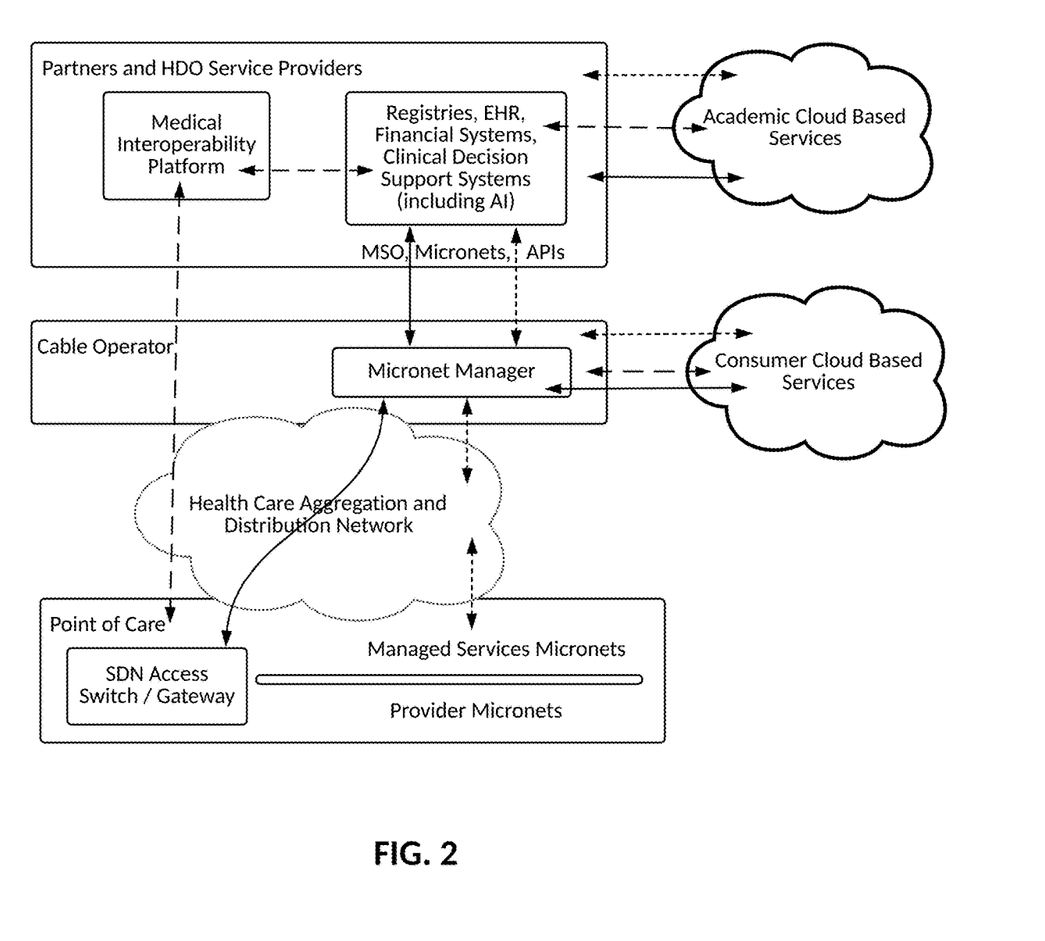
FIG. 2 is a detailed schematic of an exemplary micronet architecture, according to an embodiment.

An architecture, according to an embodiment, that involves Micronets is depicted in FIG. 2, where a medical interoperability platform is enabled to communicate with registries, the Electronic Health Record (EHR), financial systems, and clinical decision support systems including those using Artificial Intelligence (AI). The latter feature is particularly effective when used in a Cloud Computing environment, such as that shown.

At the application layer, the actual API to access services is provided by the Micronet Manager, which, in this embodiment, is hosted by a Cable Operator, which also has access to the Consumer Cloud and resources available thereon. As used herein, a Cable Operator is an example of a network operator engaged in the provision of the healthcare aggregation and distribution network.

At the network layer, the Micronet Manager is connected to the Health Care Aggregation and Distribution Network, which in turn is connected to managed services micronets, and the point-of-care micronets, including home (off-premise) micronets. The term "connected" means that the micronets in question are established in a controlled way with the Micronet Manager being granted access and control to them according to the operator's policies. The Micronet Manager instructs one or more SDN Access switches or gateways to establish necessary connections across multiple networks. Accordingly, the Micronet Manager can work with, as well as without, SDN switches by establishing connections with the pre-SDN types of switches and routers using older technologies, such as Virtual Local Area Networks (VLAN), Multiprotocol Label Switching (MPLS), Integrated Services (IntServ), etc. In this way, a Micronet Manager is capable of providing an end-to-end path between any two endpoints by communicating with the switches and gateways along the path. Some specific embodiments are described further below, and shown in FIG. 3.

Specifically in the context of the PCN, the Micronet Manager is referred to as a PCN Controller. Its function is directed by service logic programs, which include the clinically-relevant service logic (which includes AI processing) and the network-relevant service logic, which follows the state of the micronets it controls. Specifically, the state includes the SDN maps and flows connecting resources. The PCN manager can be further decomposed into a mediation and clinical state function that manages policy and a separate function that manages traffic.

Other PCN resources, managed or accessed by the PCN controller are the PCN elements proper, clinical servers, third party servers, and clinical devices. The PCN elements are servers providing registration services, API access, and/or authentication, authorization, and accounting services. Clinical servers include, but are not limited to, Clinical Decision Support System (CDSS), Point of Care, Gateway, Health Delivery Organization (HDO) Electronic Health Record (EHR), and Ambulatory Care Center EHR servers, which comprise the Primary Care Physician (PCP) EHR and Specialty Care (SC) EHR.

In a patient-centric embodiment, each patient is assigned a micronet object as he or she enters the health system. The micronet object may be self-instantiated by a patient, or, alternatively it can be created by hospital admissions personnel, a PCP or a payer. Within an established identity management system, the micronet object is pegged to the patient's identity, which can also be mapped to the patient's present network address. In a payer-centric embodiment, an insurer creates a micronet when a patient joins the insurer's system. Although not required by the methods disclosed herein, the integrity of a set of lifetime events of a micronet object can be ensured—and verified at any time—using blockchain technology to link such events and the appropriate artifacts.

The following description of an algorithm for the PCN instantiation in the episodic embodiment is provided for illustrative purposes. In the episodic embodiment, a micronet object is instantiated when a patient is submitted for care. More precisely, the Admission, Discharge, Transfer (ADT) events trigger the micronet object instantiation. In a fully-federated PCN, this step also discovers other existing micronet objects related to the patient. At this point, a patient physical ID (as derived cryptographically from the wristband material, for example) as well as a logical ID (such as a public key or its respective certificate ID) are created and cryptographically bound, for example, by the methods disclosed in U.S. Pat. No. 10,984,081 and U.S. Patent Pub. No. 2019/0394050, which are hereby incorporated by reference in their entireties. The micronet object is then bound to the patient ID, which will be used for ID-based routing and discovery. With that, the identity of the patient becomes identical to that of the respective micronet object(s) as it may be asserted by specific policies. The same procedure may apply to the Master Patient Index, or EMPI, or both. Also at this point, allocation of the resources (such as flow rule creation, or provisioning) is provided in the EHR and CDSS. If necessary, the HDO SDN network may create dynamically, by using Network Functional Virtualization (NFV), a virtual switch to be assigned to a patient. After admission, a patient is transferred to a unit and a physician specifies the appropriate workflows and resources.

In respect to software-defined networking, two polar cases—the one for a completely non-integrated networking and the one for fully-integrated networking—are described to facilitate understanding, although other use cases are also possible. In the fully-non integrated case, networking is transparent to the clinical aggregation network elements (such as gateways or platforms), and the SDN-like capabilities are provided as an overlay. This capability can be leveraged, for example, through middleware, which provides an API identical to that of the SDN. In the fully-integrated case, all networking elements are SDN-compatible and can leverage the SDN directly. Either way, because the same API is used, the operation of the network is invariant of the degree of SDN penetration as long as appropriate middleware or other adaptation software is deployed.

In an exemplary payer-centric PCN instantiation, an algorithm instructs the HDO-EHR to query the payer or interoperable network database for prior history, in which previous micronets and/or micronet objects, PCN IDs and other artifacts are obtained based on the payer's workflow having been incorporated into the system.

At least four instantiations of the PCN system, shown in FIGS. 3A, 3B, 3C and 3D, are possible:

- instantiation 1 (FIG. 3A)—single point of use: assume an SDN enabled gateway (e.g., Micronets) at the points of use (such as hospital). This instantiation is the basis for the examples disclosed above.
- instantiation 2 (FIG. 3B)—single point of use: assume an over the top (OTT) IP delivery from an out of premise SDN point of service. This instantiation is provided through tunneling or similar means over an existing network architecture without need for specific service support from that architecture at a single campus or enterprise or home network location.
- instantiation 3 (FIG. 3C)—multiple points of use: all points use SDN. Multiple points can create a federated or interoperable network of Patient Centric Networks, each with their clinical services and network control environment. For example, a hospital with its own PCN infrastructure can interwork with a service provider PCN to extend connectivity to patients not at the hospital.
- instantiation 4 (FIG. 3D)—multiple points of use: all points use OTT IP or combination of OTT IP and SDN. Again, a VPN or similar tunneling architecture can be used as described in instantiation 2 with the addition of a federated or interoperable network of PCNs.

In all of the instantiation cases, SDN is used figuratively. Any type of control architecture that manages state and connectivity automatically and programmatically can be used instead of or in addition to SDN, to include programmable routers and switching using programming APIs, such as P4. Further, any access technology that provides adequate identity of the connecting devices (to include WiFi, Bluetooth, NFC, 802.2/3, LTE including 4G and 5G, 802.15) to create a specific flow with strong identity may be used.

Figure 3A:
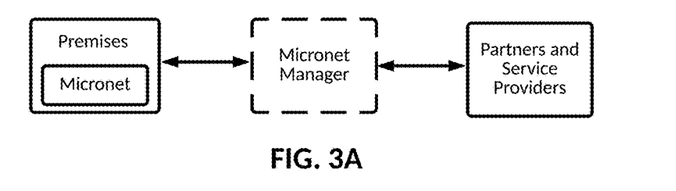
FIGS. 3A and 3B illustrate exemplary micronet platform configurations for systems having a single provider network.
Figure 3B:
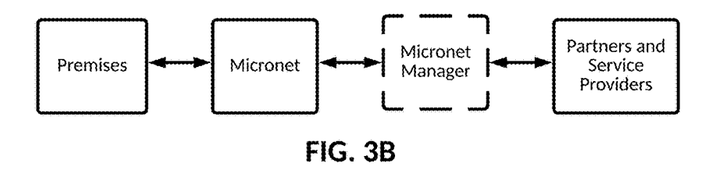
Figure 3C:
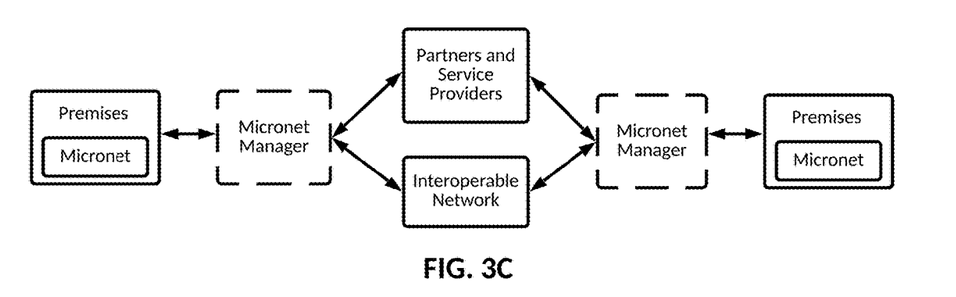
FIGS. 3C and 3D illustrate exemplary micronet platform configurations for systems comprising multiple provider networks.
Figure 3D:
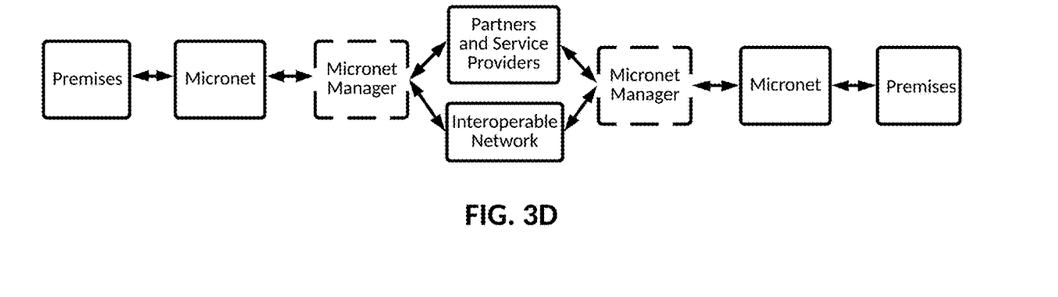

The exemplary micronet platform configurations shown in FIGS. 3A, 3B, 3C and 3D disclose premises, such as a point of care. In FIGS. 3A and 3C, a micronet is established on-premises (e.g., via a gateway, cable modem, or LTE hub). FIGS. 3B and 3D illustrate off-premise or out of premise micronet points of service, which may be connected to the point of care by a VPN or other tunneling architecture. The illustrated configurations also contemplate a micronet manager that may be off-premises, such as within a cable operator's network. The micronet provides access to and from partners and service providers, such as HDO services. In configurations involving multiple provider micronets (FIGS. 3C and 3D), an interoperable network may store information within a database, and compile, search, and distribute the information to/from multiple providers.

Methods and Apparatus for Semantic Mapping and Universal Multi-Device Support with Micronets in Patient-Centric Networks (PCN)

Systems and methods for naming, tracking, discovering, interworking, and managing a plurality of medical devices (such as blood pressure monitors, medicine pumps, etc.) according to a given policy, called semantic mapping, is now described. Semantic mapping is disclosed herein in connection with Domain Name Systems (DNS) (Mockapetris, 1987) and Software-Defined Networks (SDN), as well as Cable Lab Micronets, although any programmatic object similar to a micronet can be employed.

Semantic mapping provides a uniform mechanism for identifying, cataloguing, discovering, and administering medical devices so as to provide a patient-centric seamless health care environment. It is uniform, first of all, in that one computer language can be used to describe the mechanism, or, if several languages are being used, each of those can be compiled to a canonical representation. Semantic mapping is also uniform in that it can operate over multiple networks, including a hospital network, a home network, an operator's network, as well as a combination thereof. Finally, it is uniform in that it can interoperate the workflows of different payers. Thus, all actions of all the parties involved in medical care, including the patient, can be traced via the devices, to enforce accountability of all actions and early discovery of critical problems.

The Electronic Health Record provides a semantic mapping, described in a computer language, which describes the devices assigned to the patient. The description of each device is accompanied by a set of actions to be performed by the device, e.g., checking patient vitals at certain times of day, administering medicine at specific times, etc. Accordingly, the present invention supports full automation of all the operations of medical devices.

Figure 4:
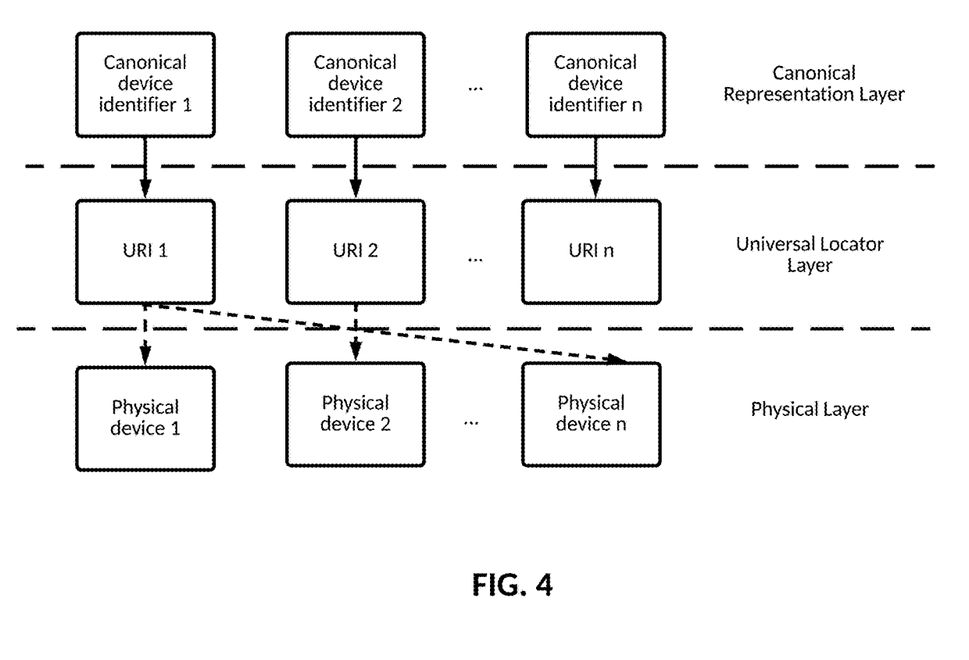
FIG. 4 is a schematic of a three-layer device identity architecture, according to an embodiment.

In an embodiment, semantic mapping specifies a three-layer naming architecture, depicted in FIG. 4.

Device names, as prescribed in the EHR, are provided in a canonical format—to be compatible with any existing specification. To achieve this, the canonical device name can, as an example, be in the form of a string:

<Medical identifier><Requirement list><Action list>, where.

<Requirement list> is the list of the parameters defining the necessary grade of the device (such as technical parameters, calibration requirements, vendor requirements, etc.) and <Action list> is a list of pairs of the time <trigger><condition list><action>.

The <trigger> specifies an event that requires an action (e.g., "systolic blood pressure is over 200," or "at 16:00", etc.). The optional <condition list> may specify other observable conditions that must hold for an action to be taken, and the <action> specifies the precise action to take place (such as "notify the doctor," "administer 0.05 mL medicine from <Device ID 2>, etc.")

Other medical requirements can be translated into a canonical name by means of a standard compiler or interpreter. Further, the above description can be implemented using such languages as extended Mark-up Language (XML), Java Script Object Notation (JSON) and others.

In the naming architecture, each of the canonical names is mapped into a unique universal resource identifier (URI) of the second layer of the architecture, by means of semantic mapping. Each URI is in turn, mapped into an existing physical device for a period of time. For example, when a non-invasive blood pressure (NIBP) device is prescribed, a patient in an emergency room may first be connected a stationary NIBP device. When the patient moves into another room, another stationary NIBP device will be connected to him or her, and this will be reflected in the value associated with the URI. That value can be obtained by translation, which will result in a record that may contain a Medium Access Component (MAC) address of the device (provided it is connected to a local area network), its IP address, serial number, room number, etc.

Figure 5:
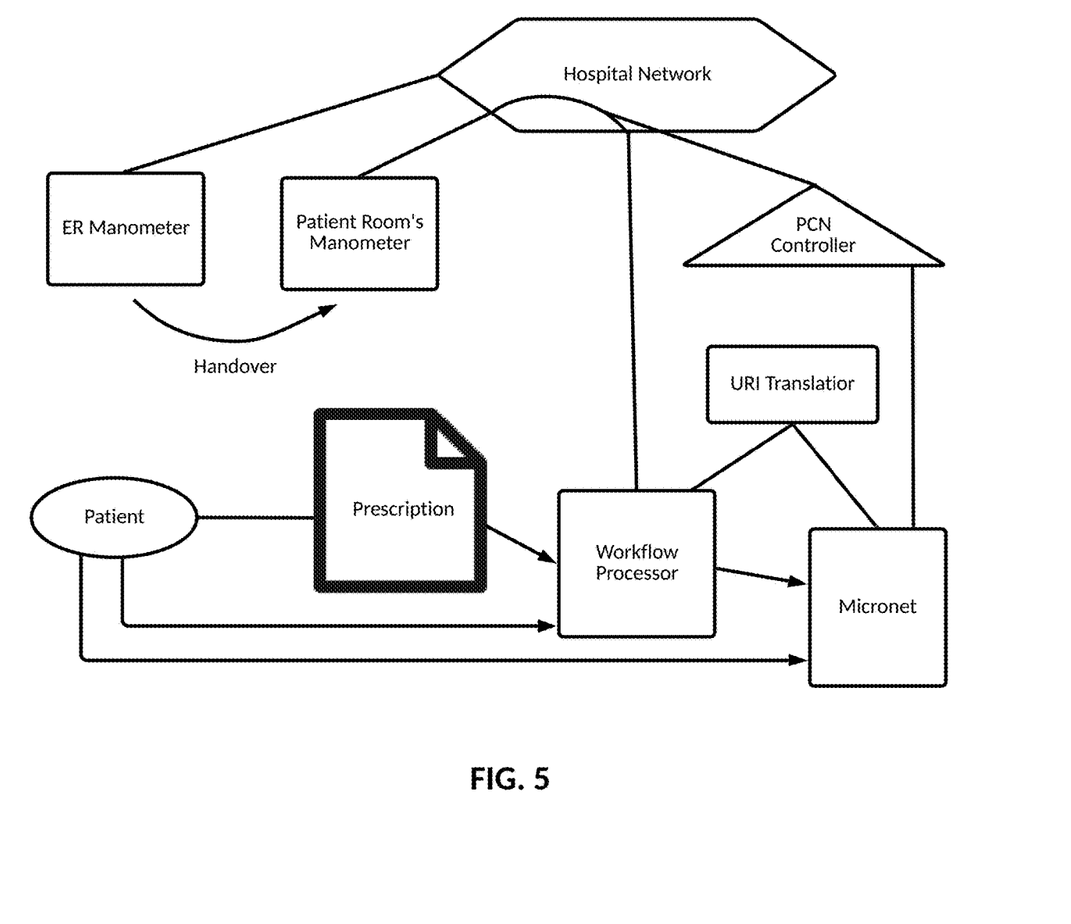
FIG. 5 demonstrates a semantic mapping operation that is being executed by a workflow processor in communication with a on-premises micronet/PCN controller, according to an embodiment.

FIG. 5 demonstrates the semantic mapping operation on a prescription for a patient that is being executed by the workflow processor that has the patient's micronet as an input. Initially, the patient was connected to an ER NIBP device. Transferring the patient to the assigned room triggered an event, which, when processed, resulted in the new translation of the URI. Consequently, the PCN Controller was instructed to establish a secure connection between the new room's NIBP and the workflow processor. With that, the association with the ER NIBP was destroyed.

Domain Name Service (DNS) may be used to perform the function of the URI Translator, although other known or specialized translators may be used. DNS is based on a standard (Mockapetris, 1987) and supports a wide range of services, including service discovery.

In FIG. 5, the PCN Controller is depicted within the hospital networking domain since no equipment here leaves the hospital. Such placement, however, is not necessary. Placing the PCN Controller in a managed network, allows for a much larger-indeed unlimited-geographic span of patient-related services owing to the ability to use software-defined networking (SDN) and similar means to establish secure and reliable connections, which are available to network operators. In addition, all other computing functions may be hosted by the network operator's Cloud (see FIG. 6).

Figure 6:
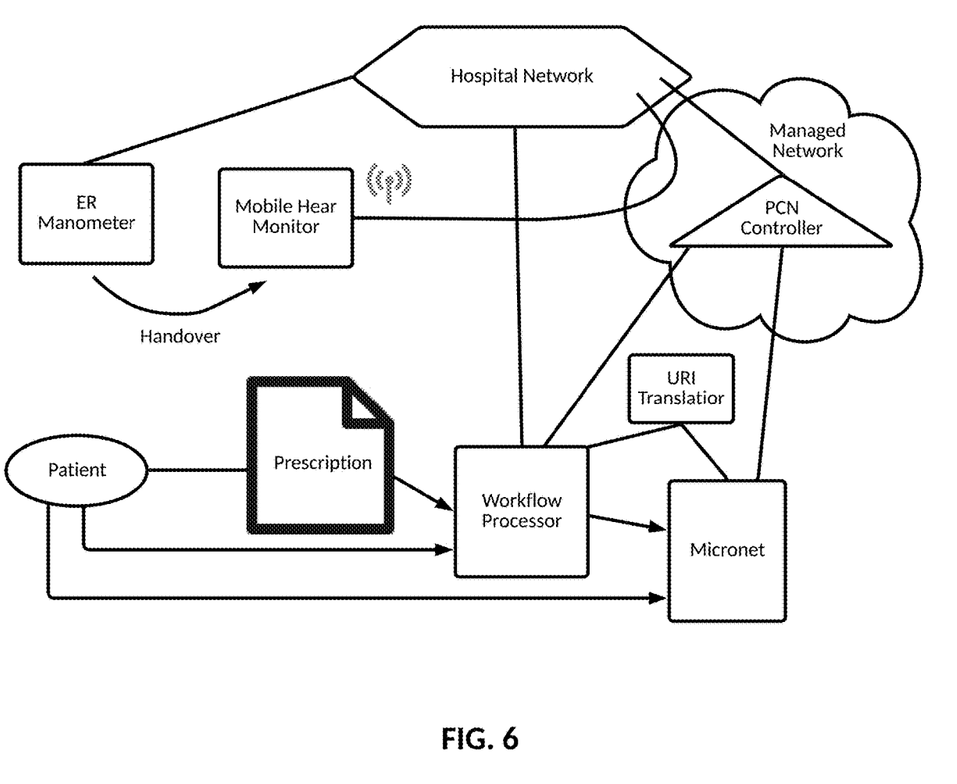
FIG. 6 demonstrates a semantic mapping operation that is being executed by a workflow processor in communication with an off-premises micronet/PCN controller, according to an embodiment.

In FIG. 6, the patient, who was initially connected to an ER heart monitor, has been discharged and given a mobile heart monitor. As the monitor's URI has been updated, the PCN Controller establishes its secure connection either directly to the monitor over a mobile network or, for example, indirectly via the patient's phone being connected to the mobile network and tethering the monitor to the patient's phone via BlueTooth. Similarly, the monitor can be directly or indirectly connected later to the patient's home network, which may be connected to an external communication network.

Method and Apparatus for Identity Management in Patient-Centric Network (PCN)

Systems and methods for maintaining the life-cycle of an identity associated with a micronet, protecting private information related to such an identity, and providing authentication and authorization methods related to the identity are now described.

Each of the above aspects involves identities, such as the identities of the patients, the identities of one or more healthcare providers, and the identities of one or more payers. The respective identifiers, along with the specific authentication and authorization requirements, the mechanisms to support those, and the policies governing the operation of authentication and authorization, are independent in different realms. Each domain (e.g., a health care provider, a hospital, or an insurance company) carries the business process through its own workflow, which is unaware of the workflows in other domains, which lends itself to compatibility and efficiency issues in traditional systems. Here, the federation of identities allows for cross-platform interactions.

Systems and methods disclosed herein support identity management, which involves maintaining the life time of identities, identity-based authentication, authorization to access resources associated with the identity, and protection of private information.

Figure 7:
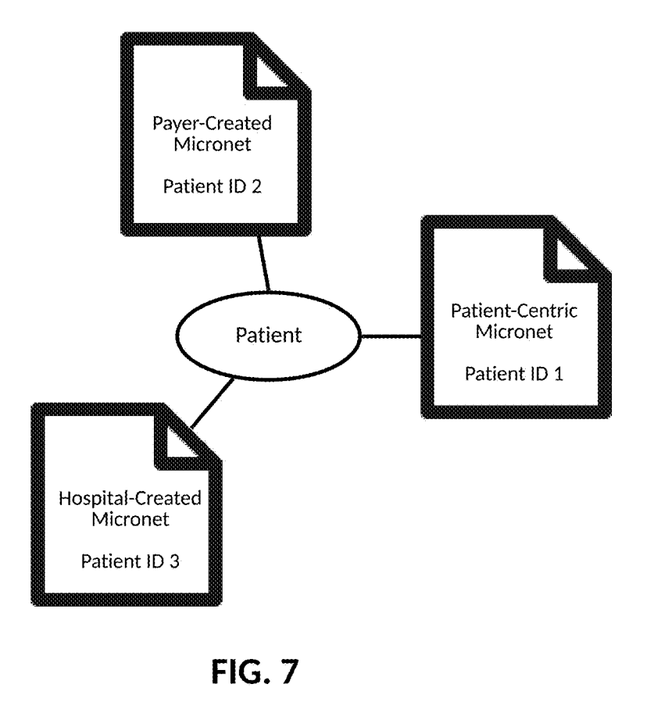
FIG. 7 is a schematic showing examples of three types of micronets.

The present systems and methods may be implemented on local networks, but are most powerful when implemented on extended or global networks. Thus, a cable or telecommunications operator may be in the best position to provide micronet management. Examples of three types of micronets are depicted in FIG. 7. Here, each micronet has a unique identity. Certain objectives of the identity management disclosed herein include: the ability to link all the identities that belong to the same patient such that the micronets reflect the patient's history, the ability to record correctly and, consequently, to recognize the state of each specific micronet in its life time, the ability to exercise proper access control to resources identified in an active micronet by an authorized entity, and the ability to protect—when required by a policy or by law—the personally identifiable information (PII) or HIPAA Protected Health Information (PHI). (HIPAA Guidance, "Guidance Regarding Methods for De-identification of Protected Health Information in Accordance with the Health Insurance Portability and Accountability Act (HIPAA) Privacy Rule", www.hhs.gov/hipaa/for-professionals/privacy/special-topics/de-identification/index.html, accessed Apr. 27, 2019.) The last of the above requirements strongly suggests that the identities involved be different from a patient's name or any other obvious identifier. Yet, the other requirements point to the necessity of the discovery of other micronets.

Figure 8:
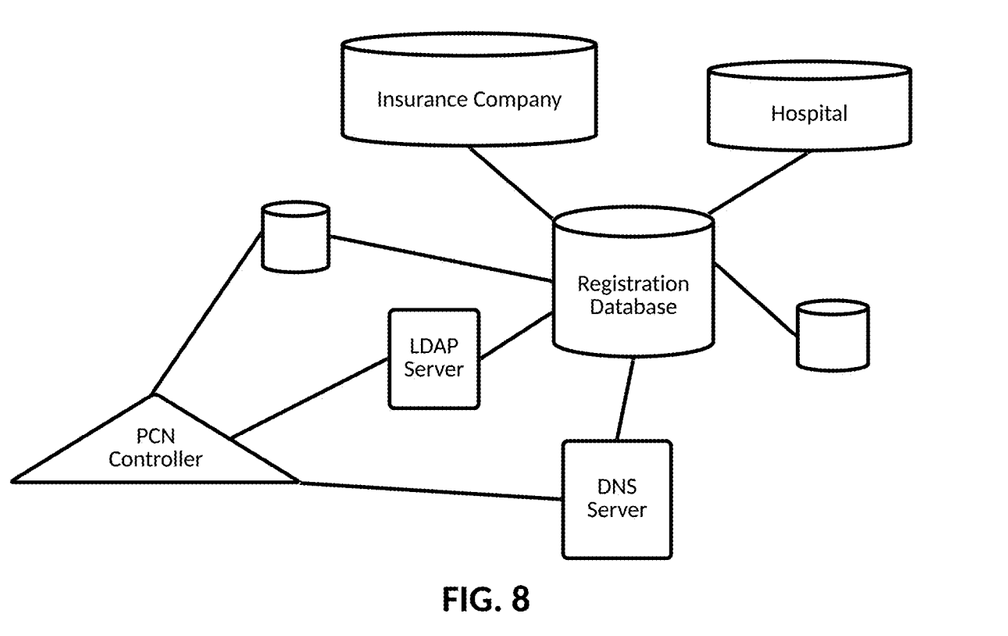
FIG. 8 is a schematic of an exemplary PCN apparatus, according to an embodiment.

An exemplary apparatus for carrying out the federation of identifies is depicted in FIG. 8. Here, at the beginning of the life cycle of a micronet object, it is assigned an identifier and deposited into a database, which may belong to a hospital, a payer (an insurance company), or some other entity. At the time of the creation of the micronet, it is registered in a central database. The word "central" means here only that the access to the database is uniform whereas it can actually be implemented as a distributed database, preferably with high-availability servers. In an embodiment, the registration database may be trusted both to associate an identity in the micronet to another discoverable identity and to control access to its records so as to allow access only to entities that have permissions to do so and only as determined by the respective scopes of such permissions. There are well-known mechanisms for achieving authorized access, such as Kerberos tickets (Faynberg, Igor and Hui-Lan Lu 2010. "Identity management services provided by network operator." Bell Labs Technical Journal. 2010; DOI: 10.1002/bltj.20426) and OAuth 2.0 tokens (IETF RFC 6749 "The OAuth 2.0 Authorization Framework" (2012), available at www.tools.ietf.org/html/rfc6749, accessed Jun. 21, 2021). Further, the registration database may be accessible, for example, through a Light-Weight Directory Protocol (LDAP) Server or a DNS server, or both.

In an embodiment, a search for all relevant micronet objects is performed by a PCN controller, and such a search may be triggered by any action in the life cycle of a micronet, particularly the creation of a new micronet. The PCN controller, when depositing a newly-created micronet object into an appropriate database, may update the information needed for discovery. This can be achieved by updating the Discovery Database itself, via the LDAP server and/or via the DNS server. The registration database and other entities may be updated by another principal based on the specific life-cycle event.

Figure 9:
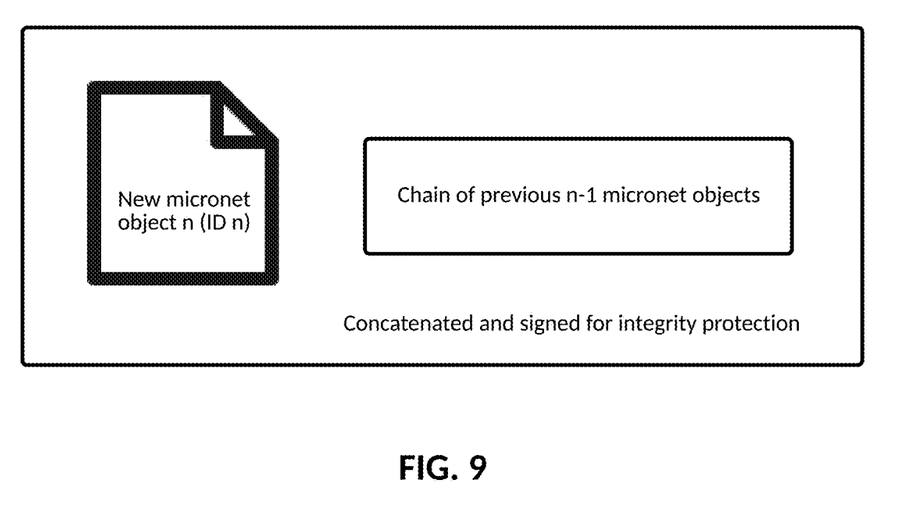
FIG. 9 is a schematic of a micronet object being added to chain of previous n-1 micronet objects, according to an embodiment.

Finally, service-chaining can be performed on a subset of micronet objects, which may eliminate a need for the discovery of all but the last micronet object created for the same patient. As depicted in FIG. 9, upon the discovery of a chain consisting of previous n-1 micronet objects (with n>1), the newly created n-th micronet object, can be added to this chain, as a minimum, by the integrity protection of its concatenation with the chain. The integrity protection can be effected by the electronic signature of the entity that has created the new object. Solely for the purpose of illustration, the signature is to be applied to the hash of the concatenation. In another embodiment, the signature may be applied to the whole concatenated object. The entity that signs the chain (e.g., the PCN Controller) must be trusted. This can be achieved using a Public Key Infrastructure (PKI), with the signing entity being given a recognizable X.509 certificate.

Figure 10:
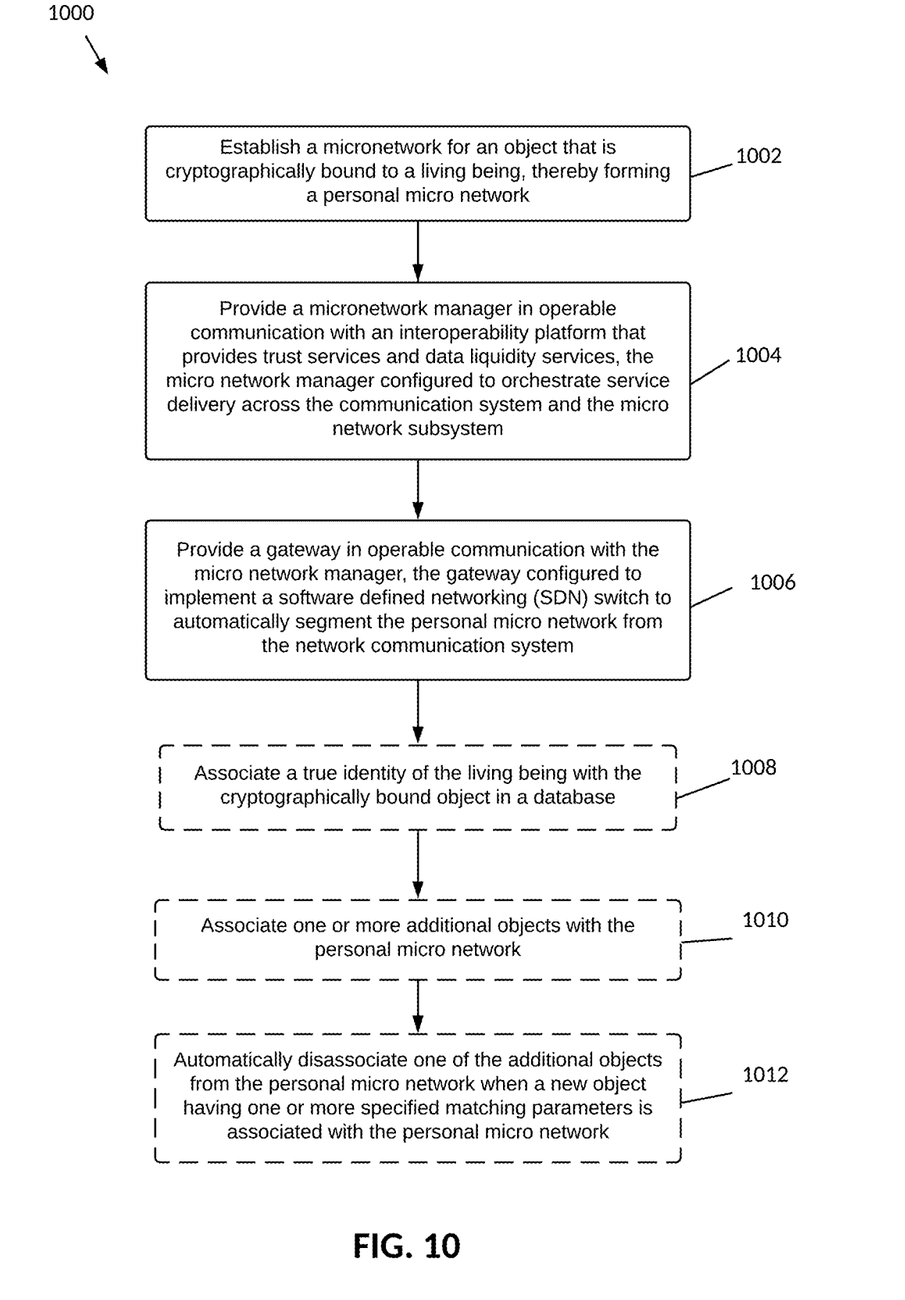
FIG. 10 is a flowchart illustrating exemplary steps in a method for securely delivering personal electronic information across wired and/or wireless media in a micro network subsystem of a network communication system.

FIG. 10 is a flowchart 1000 illustrating exemplary steps in a method for securely delivering personal electronic information across wired and/or wireless media in a micro network subsystem of a network communication system. The method begins, at step 1002, by establishing a micro network for an object that is cryptographically bound to or cryptographically associated with a living being, thereby forming a personal micro network. In step 1004, a micro network manager in operable communication with an interoperability platform provides trust services and data liquidity services. The micro network manager is configured to orchestrate service delivery across the communication system and the micro network subsystem. In step 1006, a gateway in operable communication with the micro network manager implements software defined networking (SDN) to automatically segment the personal micro network from the network communication system. Steps 1008-1012 are optional. Step 1008 involves associating a true identity of the living being with the cryptographically bound object in a database. In step 1010, one or more additional objects are associated with the personal micro network. In step 1012, one of the additional objects is automatically disassociated from the personal micro network when a new object having one or more specified matching parameters is associated with the personal micro network.

The embodiments herein may be implemented in a variety of ways as a matter of design choice. In this regard, the invention can take the form of an entirely hardware embodiment, an entirely software embodiment or an embodiment containing both hardware and software elements. In an embodiment, the invention is implemented in software, which includes but is not limited to firmware, resident software, microcode, etc. Furthermore, the invention can take the form of a computer program product accessible from the computer readable medium providing program code for use by or in connection with a computer or any instruction execution system. For the purposes of this description, the computer readable medium can be any apparatus that can tangibly store the program for use by or in connection with the instruction execution system, apparatus, or device, including the computer system.

The medium can be any tangible electronic, magnetic, optical, electromagnetic, infrared, or semiconductor system (or apparatus or device). Examples of a computer readable medium include a semiconductor or solid state memory, magnetic tape, a removable computer diskette, a random access memory (RAM), a read-only memory (ROM), a rigid magnetic disk and an optical disk. Some examples of optical disks include compact disk-read only memory (CD-ROM), compact disk-read/write (CD-R/W) and DVD.

The computing system, suitable for storing and/or executing program code, can include one or more processors coupled directly or indirectly to memory through a system bus. The memory can include local memory employed during actual execution of the program code, bulk storage, and cache memories which provide temporary storage of at least some program code in order to reduce the number of times code is retrieved from bulk storage during execution. Input/output (I/O) devices (including but not limited to keyboards, displays, pointing devices, etc.) can be coupled to the system either directly or through intervening I/O controllers. Network adapters may also be coupled to the system to enable the computing system to become coupled to other data processing systems, such as through host systems interfaces, or remote printers or storage devices through intervening private or public networks. Modems, cablemodem and Ethernet cards are just a few of the currently available types of network adapters.

Statements Regarding Incorporation by Reference and Variations

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments, exemplary embodiments and optional features, modification and variation of the concepts herein disclosed can be resorted to by those skilled in the art, and that such modifications and variations are considered to be within the scope of this invention as defined by the appended claims. The specific embodiments provided herein are examples of useful embodiments of the invention and it will be apparent to one skilled in the art that the invention can be carried out using a large number of variations of the devices, device components, and method steps set forth in the present description. As will be apparent to one of skill in the art, methods, software and apparatus/devices can include a large number of optional elements and steps. All art-known functional equivalents of materials and methods are intended to be included in this disclosure. Nothing herein is to be construed as an admission that the invention is not entitled to antedate such disclosure by virtue of prior invention.

When a group of substituents is disclosed herein, it is understood that all individual members of that group and all subgroups are disclosed separately. When a Markush group or other grouping is used herein, all individual members of the group and all combinations and subcombinations possible of the group are intended to be individually included in the disclosure.

It must be noted that as used herein and in the appended claims, the singular forms "a", "an", and "the" include plural reference unless the context clearly dictates otherwise. Thus, for example, reference to "a processor" includes a plurality of such processors and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is/are not specifically disclosed herein.

What is claimed is:

1. A network communication system implementing a micronet subsystem for (a) securely delivering personal electronic information across wired and/or wireless media and (b) organizing one or more connected devices within a plurality of trust domains defining a plurality of micronets, respectively, the network communication system comprising:
    a partner network including an interoperability platform that provides trust services and data liquidity services for the micronet subsystem;
    a micronet manager in operable communication with the interoperability platform and configured to orchestrate service delivery across the network communication system and the micronet subsystem;
    a gateway in operable communication with the micronet manager, the gateway configured to implement a software defined networking (SDN) switch to automatically segment a provider network into SDN-based first and second personal micronets of the plurality of micronets, configured to be established for an object that is cryptographically bound to a living being; and
    a database that registers the true identity of the living being with the cryptographically bound object,
    wherein the first personal micronet defines a first trust domain for the cryptographically bound object with respect to the partner network that enables a first level of access with the partner network,
    wherein the second personal micronet defines a second trust domain for the cryptographically bound object with respect to the partner network that enables a second level of access with the partner network,
    wherein the first level of access is different from the second level of access.

2. The network communication system of claim 1, wherein the micronet manager is located in the provider network or in a system operator network.

3. The network communication system of claim 1, wherein the gateway is located in the provider network or remote from the provider network.

4. The network communication system of claim 1, wherein the interoperability platform is a medical interoperability platform facilitating data services from one or more of the database, an electronic health record database, a medical financial system, clinical decision support systems, and academic cloud services.

5. The network communication system of claim 1, wherein the cryptographically bound object is selected from the group consisting of a bar code, a QR code, a radio frequency ID (RFID) tag, a Bluetooth device, a near-field communication device, a Wi-Fi enabled device, and/or a personal computing device.

6. The network communication system of claim 1, further comprising one or more additional objects associated with at least one of the first and second personal micronets.

7. The network communication system of claim 6, wherein the one or more additional objects include medical provisions selected from the group consisting of a medical device, a medical provider, a medical payer, a prescription, a diagnosis, a bill, or a treatment protocol.

8. The network communication system of claim 6, wherein at least one of the additional objects comprises a canonical name including at least an object identifier and an object parameter list.

9. The network communication system of claim 8, wherein the canonical name further comprises an action list including instructions that when executed by a processor cause a respective additional object to perform a function.

10. The network communication system of claim 8, further comprising a translator for converting the canonical name into instructions for a workflow processor of the provider network.

11. The network communication system of claim 1, wherein the database is an interoperable network database that compiles multiple objects cryptographically bound to each of the living beings by a plurality of provider networks and generates a comprehensive lifetime record of events.

12. A method for securely delivering personal electronic information across wired and/or wireless media in a micronet subsystem of a network communication system configured to organize one or more connected devices within a plurality of software-defined networking (SDN)- based trust domains defining a plurality of micronets, respectively, the method comprising the steps of:
- establishing a first micronet for an object that is cryptographically bound to a living being, thereby forming a first personal micronet defined by a first trust domain of the plurality of trust domains;
- providing a micronet manager in operable communication with an interoperability platform that provides trust services and data liquidity services, the micronet manager configured to orchestrate service delivery across the network communication system and the micronet subsystem;
- providing a gateway in operable communication with the micronet manager, the gateway configured to implement a software defined networking (SDN) switch to automatically segment the first personal micronet from the network communication system; and
- establishing a second micronet for the cryptographically bound object, thereby forming a second personal micronet defined by a second trust domain of the plurality of trust domains,
- wherein the first personal micronet defines a first level of access with the network communication system using the cryptographically bound object,
- wherein the second personal micronet defines a second level of access with the network communication system using the cryptographically bound object,
- wherein the first level of access is different from the second level of access.

13. The method of claim 12, further comprising a step of associating a true identity of the living being with the cryptographically bound object in a database.

14. The method of claim 12, wherein the personal information is medical information.

15. The method of claim 12, wherein the cryptographically bound object is selected from the group consisting of a bar code, a QR code, a radio frequency ID (RFID) tag, a Bluetooth device, a near-field communication device, a Wi-Fi enabled device, and/or a personal computing device.

16. The method of claim 12, further comprising a step of associating one or more additional objects with the personal micronet.

17. The method of claim 16, wherein the one or more additional objects include medical provisions selected from the group consisting of a medical device, a medical provider, a medical payer, a prescription, a diagnosis, a bill, or a treatment protocol.

18. The method of claim 16, wherein at least one of the additional objects comprises a canonical name including at least an object identifier and an object parameter list.

19. The method of claim 18, further comprising a step of automatically disassociating one of the additional objects from the personal micronet when a new object having one or more specified matching parameters is associated with the personal micronet.

20. The method of claim 18, wherein the canonical name further comprises an action list including instructions that, when executed by a processor, cause the additional object to perform a function.

* * * * *